United States Patent [19]

Anello et al.

[11] 4,337,361

[45] Jun. 29, 1982

[54] LIQUID PHASE SYNTHESIS OF HEXAFLUOROACETONE

[75] Inventors: Louis G. Anello, Hamburg; Michael Van Der Puy, Cheektowaga; Martin A. Robinson, East Amherst; Richard E. Eibeck, Orchard Park, all of N.Y.

[73] Assignee: Allied Corporation, Morris Township, Morris County, N.J.

[21] Appl. No.: 238,920

[22] Filed: Feb. 27, 1981

[51] Int. Cl.$^3$ ............................................. C07C 45/56
[52] U.S. Cl. ................................................... 568/386
[58] Field of Search ................ 568/386, 407, 399, 400

[56] References Cited

U.S. PATENT DOCUMENTS

| 3,006,973 | 10/1961 | Hauptschein et al. | 568/407 |
|---|---|---|---|
| 3,257,457 | 6/1966 | Anello et al. | 568/394 |
| 3,367,971 | 2/1968 | Madison | 568/407 |
| 3,391,119 | 7/1968 | Anderson | 568/386 |
| 4,057,584 | 11/1977 | Touzuka et al. | 568/399 |

OTHER PUBLICATIONS

Middleton et al., J. Org. Chem., vol. 30, pp. 1384-1390 (1965).
Martin, J. Chem. Soc., pp. 2944-2947 (1964).
Kitayuma et al., Chemical Letters, pp. 267-271 (1973).

Primary Examiner—Natalie Trousof
Assistant Examiner—James H. Reamer
Attorney, Agent, or Firm—Thomas D. Hoffman; Jay P. Friedenson

[57] ABSTRACT

A process for the preparation of hexafluoroacetone which comprises contacting, in the liquid phase, hexafluorothioacetone dimer in the presence of an aprotic solvent containing a catalytic amount of an alkali metal fluoride with a gaseous oxidant selected from the group consisting of air, $O_2$, $O_3$, $NO_2$ and $NO$ is disclosed. The preferred aprotic solvent is dimethylformamide, and the preferred gaseous oxidant is $O_2$.

10 Claims, No Drawings

LIQUID PHASE SYNTHESIS OF HEXAFLUOROACETONE

BACKGROUND OF THE INVENTION

The present invention relates to a process for preparing hexafluoroacetone by contacting, in the liquid phase, hexafluorothioacetone dimer with a gaseous oxidant such as $O_2$ in the presence of a catalytic amount of an alkali metal halide and an aprotic solvent such as dimethylformamide.

Hexafluoroacetone is a known compound useful as an intermediate in the preparation of hexafluoropropanol and hexafluoroisobutylene, and for the preparation of compounds containing the $(CF_3)_2C-$ group.

W. J. Middleton et al. (*J. Org. Chem.*, 30, 1384–1390 (1965)) disclose preparation of hexafluoroacetone by gas phase oxidation of hexafluorothioacetone dimer with nitric oxide, NO, at 650° C., over quartz in a Vycor tube. However, this reference reports that nitric oxide does not react with hexafluorothioacetone dimer at low temperature, and that oxygen, which is also unreactive at lower temperatures, reacts with hexafluorothioacetone dimer at 650° C. to give only high conversion thereof into carbonyl fluoride and sulfur dioxide, but no hexafluoroacetone.

U.S. Pat. Nos. 3,164,637 and 3,257,457 (L. G. Anello et al.) disclose preparation of hexafluoroacetone by high temperature, gas phase fluorination of hexachloroacetone with HF in the presence of a chromium catalyst.

U.S. Pat. No. 4,057,584 (T. Touzuka et al.) discloses preparation of hexafluoroacetone by gas phase oxidation of perfluoropropene with oxygen over a fluorinated alumina catalyst.

These prior art preparations operate in the gas phase, employ high temperature, special equipment and specially treated catalysts.

In the presence of fluoride ion, hexafluorothioacetone dimer in dimethylformamide is in equilibrium with monomeric hexafluorothioacetone (T. Kitazume et al. *Chemistry Letters*, 267 (1973)).

Accordingly, there is a need for an economical process for the preparation of hexafluoroacetone which operates at convenient temperatures without special equipment or expensive catalysts.

It is an object of the present invention to provide a process for a liquid phase preparation of hexafluoroacetone at low temperature. This and other objects and advantages of the present invention will become obvious from the following description.

SUMMARY OF THE INVENTION

The present invention includes a process for the preparation of hexafluoroacetone which comprises contacting, in the liquid phase, hexafluorothioacetone dimer in the presence of an aprotic solvent containing a catalytic amount of an alkali metal fluoride with a gaseous oxidant selected from the group consisting of air, $O_2$, $O_3$, $NO_2$, and NO.

DETAILED DESCRIPTION OF THE PRESENT INVENTION AND OF THE PREFERRED EMBODIMENTS

The present invention provides a convenient liquid phase synthesis of hexafluorothioacetone in the presence of an aprotic solvent, preferably dimethylformamide, containing a catalytic amount of an alkali metal fluoride with a gaseous oxidant selected from the group consisting of air, $O_2$, $O_3$, $NO_2$, and NO under surprisingly milder temperature conditions than disclosed by the prior art for a time sufficient to produce hexafluoroacetone. In accordance with the present invention, a selected gaseous oxidant is contacted with a liquid phase solution of the hexafluorothioacetone dimer in an aprotic solvent containing catalytic amounts of alkali metal fluoride, at liquid phase temperatures of no more than about 200° C., preferably between about 75° and 200° C., more preferably between about 100° and 135° C., to achieve high conversions of hexafluorothioacetone dimer and high yields of hexafluoroacetone.

While the gaseous oxidant useful in the present invention is selected from the group consisting of air, $O_2$, $O_3$, NO and $NO_2$, diluents such as $N_2$ can be present so long as they do not interfere with the oxidation of the present reaction. For economic reasons, $O_2$ in air is the preferred oxidant.

The molar ratios of hexafluorothioacetone dimer to gaseous oxidant, listed in the following table, are the minimum preferred ratios conveniently employed to fulfill the stoichiometry of each oxidation reaction of hexafluorothioacetone dimer in a selected aprotic solvent containing a catalytic amount of alkali metal fluoride.

| Molar Ratios Hexafluorothioacetone dimer:oxidant |
| --- |
| 1:1 for $O_2$ |
| 1:1 for $O_3$ |
| 1:2 for NO |
| 1:1 for $NO_2$ |

A slight excess, e.g. 10–20 mole %, of oxidant and/or dimer can be employed in each above-listed ratio without affecting the product composition or yield of hexafluoroacetone. In the case of the $O_2$, it is preferred to use a molar ratio of hexafluorothioacetone dimer to $O_2$ equal to about 1:1. In the case of the $NO_2$ it is preferred to use a molar ratio of hexafluorothioacetone dimer to $NO_2$ equal to about 1:1.

The term "aprotic solvents" includes those solvents which dissolve at least a catalytic amount of alkali metal fluoride and the organic materials, e.g., hexafluorothioacetone dimer used in the present invention. Such aprotic solvents comprise lower alkyl nitriles, lower alkyl tertiary amides, especially lower alkyl tertiary formamides and lower alkyl tertiary acetamides, lower alkyl sulfoxides, lower alkyl sulfones and N-lower alkyl pyrrolidones. The aprotic solvents found useful for the present reaction include those aprotic solvents selected from the group of acetonitrile, dimethacetamide, dimethylformamide, dimethyl sulfoxide and N-methyl pyrrolidone. Dimethylformamide is the preferred aprotic solvent.

The concentration of the hexafluorothioacetone dimer in the selected aprotic solvent is not critical. Sufficient aprotic solvent should be present to provide a homogeneous solvent of said dimer.

Among the alkali metal fluorides found useful in catalyzing the dissociation of hexafluorothioacetone dimer dissolved in a selected aprotic solvent, are LiF, NaF, KF and CsF. For economic reasons, KF is preferred. The catalytic amount of alkali metal fluoride, preferably KF, found effective in dissociating hexafluorothioacetone dimer into hexafluorothioacetone monomer in a selected aprotic solvent varies from at least about 0.06 to about 1.0 moles of alkali metal fluoride per mole of hexafluorothioacetone dimer. While an amount of alkali metal fluoride in excess of 1.0 mole per mole of hexafluorothioacetone dimer is effective in catalyzing the formation of hexafluorothioacetone monomer, the preferred molar ratio of alkali metal fluoride to hexafluorothioacetone dimer is at least about 0.06:1 to about 1:1.

Anhydrous KF in dimethylformamide containing no more than about 0.05% by weight water is most preferred. In a specific embodiment of the present invention, the reactants and apparatus are substantially water free; KF is made essentially anhydrous conveniently by vacuum drying; and dimethylformamide is treated with an appropriate drying agent to produce dimethylformamide having no more than about 0.05% by weight water.

In another specific embodiment of the present invention, the hexafluoroacetone produced is recovered by subjecting the gaseous effluent stream from the reaction mixture to sufficiently high pressures and low temperature to condense hexafluoroacetone (bp −28° C.). Further purification of the hexafluoroacetone can conveniently be achieved by fractional distillation.

The following examples illustrate and describe but do not limit the present invention. The scope of the present invention is to be interpreted only in view of the appended claims.

EXAMPLE I

Into a 250 mL, 3 neck flask fitted with a thermometer, stirrer, gas inlet tube and a condenser cooled to −20° C. and connected to a dry ice-acetone cooled trap were charged 125 g (0.344 mole) of 85% pure hexafluorothioacetone dimer

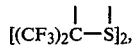

3.5 g (0.06 mole) of anhydrous KF and 100 mL of dimethylformamide. The mixture was heated to 110° C. and oxygen was passed in over a period of 14 hours. There was recovered 55.5 g (0.335 mole) of hexafluoroacetone in the −78° C. trap for a 57% conversion and yield. There were also recovered 21.6 g (0.67 mole) of elemental sulfur for a 100% yield.

EXAMPLE II

Following the procedure of Example I, 125 g (0.344 mole) of 85% pure

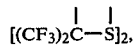

1.5 g (0.026 mole) of anhydrous KF, and 100 mL of dimethylacetamide were charged to the reaction flask of Example I. The mixture was heated to 110° C. and oxygen was passed in over a 10 hr. period. There were recovered 10.5 g (0.063 mole) of hexafluoroacetone in the −78° C. trap for a 11% conversion and yield.

EXAMPLE III

Following the procedure of Example I, 125 g (0.344 mole) of

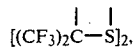

3.0 g (0.052 mole) of anhydrous KF and 100 mL of dimethylformamide were charged to the reaction flask. The mixture was heated to 110° C. and 11 g (0.37 mole) NO, nitric oxide, were passed subsurface to the reaction mixture during a 12 hour period. There were recovered 49 g (0.295 mole) hexafluoroacetone in the −78° C. trap for a 43% conversion and yield.

EXAMPLE IV

Following the procedure of Example I, 125 g (0.344 mole)

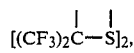

3.0 g (0.052 mole) anhydrous KF and 100 mL of dimethylformamide were charged to the reaction flask. The mixture was heated to 100°–140° C. and nitrogen dioxide was passed subsurface to the reaction mixture. There were recovered 77.3 g (0.465 mole) hexafluoroacetone in the −78° C. trap for a 67.5% conversion and yield.

EXAMPLE V

Following the previously described procedure of Example I, 50 g (0.14 mole) of

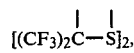

1.5 g (0.026 mole) of KF and 30 mL of DMF were charged to the reaction flask of Example I. The mixture was heated to 110° C. and dry air was passed subsurface to the reaction mixture over an 8 hour period. There were recovered 11 g (0.066 mole) of hexafluoroacetone in the −78° C. trap for a 23.6% conversion and yield.

EXAMPLE VI

Following the previously described procedure of Example I, 50 g (0.14 mole) of

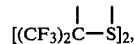

1.5 g (0.026 mole) of KF and 30 mL of DMF are charged to the reaction flask of Example I. The mixture is heated to 110° C. and ozone from a commercial ozonator is passed subsurface to the reaction mixture over a 10 hour period. There is recovered hexafluoroacetone in the −78° C. trap.

EXAMPLES VII–X

In the following examples, the process of Example I is repeated excepting that the aprotic solvent is varied as follows: dimethylacetamide (VII), acetonitrile (VIII), dimethyl sulfoxide (IX) and N-methyl pyrrolidone (X).

EXAMPLES XI–XIV

In the following examples, the process of Example III is repeated excepting that the aprotic solvent is varied as follows: dimethylacetamide (XI), acetonitrile (XII), dimethyl sulfoxide (XIII) and N-methyl pyrrolidone (XIV).

EXAMPLES XV–XVIII

In the following examples, the process of Example IV is repeated excepting that the aprotic solvent is varied as follows: dimethylacetamide (XV), acetonitrile (XVI), dimethyl sulfoxide (XVII) and N-methyl pyrrolidone (XVIII).

EXAMPLES XIX–XXII

In the following examples, the process of Example V is repeated excepting that the aprotic solvent is varied as follows: dimethylacetamide (XIX), acetonitrile (XX), dimethyl sulfoxide (XXI) and N-methyl pyrrolidone (XXII).

EXAMPLES XXIII–XXV

In the following examples, the process of Example I is repeated excepting that the alkali metal fluoride is varied as follows: LiF (XXIII), NaF (XXIV), and CsF (XXV).

We claim:

1. A process for the preparation of hexafluoroacetone which comprises contacting, in the liquid phase, hexafluorothioacetone dimer in the presence of an aprotic solvent containing a catalytic amount of an alkali metal fluoride with a gaseous oxidant selected from the group consisting of air, $O_2$, $O_3$, $NO_2$ and NO.

2. The process of claim 1 wherein the aprotic solvent is selected from the group consisting of acetonitrile, dimethylacetamide, dimethylformamide, dimethyl sulfoxide and N-methyl pyrrolidone.

3. The process of claim 2 wherein the aprotic solvent is dimethylformamide.

4. The process of claim 3 wherein the alkali metal fluoride is KF and wherein the molar ratio of said dimer:KF is at least about 1:0.06 to about 1:1.

5. The process of claim 4 wherein the temperature of the liquid phase is between 75° and 200° C.

6. The process of claim 4 wherein the temperature of the liquid phase is between about 100° and 135° C.

7. The process of claim 4, 5 or 6 wherein the oxidant is $O_2$ and wherein the molar ratio of said dimer:$O_2$ is about 1:1.

8. The process of claim 5 or 6 wherein the oxidant is NO and wherein the molar ratio of said dimer:NO is about 1:2.

9. The process of claim 5 or 6 wherein the oxidant is $NO_2$ and wherein the molar ratio of said dimer:$NO_2$ is about 1:1.

10. The process of claim 2 which further comprises recovering hexafluoroacetone from a gaseous effluent stream containing same by condensing said effluent stream under sufficiently high pressure and low temperature to condense hexafluoroacetone.

* * * * *